United States Patent
Allison

(10) Patent No.: US 12,161,403 B2
(45) Date of Patent: Dec. 10, 2024

(54) SYSTEMS AND METHODS FOR MICROWAVE ABLATION AND MEASURING TEMPERATURE DURING ABLATION

(71) Applicant: BH Scientific, LLC, Rancho Palos Verdes, CA (US)

(72) Inventor: Robert C. Allison, Rancho Palos Verdes, CA (US)

(73) Assignee: BH Scientific, LLC, Rancho Palos Verdes, CA (US)

( * ) Notice: Subject to any disclaimer, the term of this patent is extended or adjusted under 35 U.S.C. 154(b) by 383 days.

(21) Appl. No.: 17/664,413

(22) Filed: May 22, 2022

(65) Prior Publication Data

US 2022/0280232 A1    Sep. 8, 2022

Related U.S. Application Data

(63) Continuation of application No. 16/424,414, filed on May 28, 2019, now Pat. No. 11,337,756.

(60) Provisional application No. 62/678,935, filed on May 31, 2018.

(51) Int. Cl.
*A61B 18/18* (2006.01)
*A61B 18/00* (2006.01)

(52) U.S. Cl.
CPC .............. *A61B 18/1815* (2013.01); *A61B 2018/00577* (2013.01); *A61B 2018/00791* (2013.01); *A61B 2018/1823* (2013.01); *A61B 2018/1838* (2013.01); *A61B 2018/1861* (2013.01)

(58) Field of Classification Search
None
See application file for complete search history.

(56) References Cited

U.S. PATENT DOCUMENTS

| 4,190,053 A | 2/1980 | Sterzer |
| 4,240,445 A | 12/1980 | Iskander et al. |
| 5,344,435 A | 9/1994 | Turner et al. |

(Continued)

FOREIGN PATENT DOCUMENTS

| CN | 205073020 U | 3/2016 |
| EP | 2299540 B1 | 1/2013 |

(Continued)

OTHER PUBLICATIONS

International Search Report & Written Opinion dated Jun. 22, 2021 in Int'l PCT Patent Appl. Serial No. PCT/IB2021/050682 (0310).

(Continued)

*Primary Examiner* — Sean W Collins
*Assistant Examiner* — Nora W Rhodes
(74) *Attorney, Agent, or Firm* — Greenberg Traurig, LLP; Christopher C. Bolten; Albert K. Heng

(57) ABSTRACT

An exemplary microwave ablation system is provided. The system may use a switching antenna for both microwave heating of target tissue and microwave radiometry to monitor the temperature of the heated tissue to ensure that the desired temperatures are delivered to adequately treat the target tissue and achieve therapeutic goals. The system may integrate switching components into the switching antenna, which eliminates error from heating of the reference termination and heating of the electrical cables.

24 Claims, 10 Drawing Sheets

(56) References Cited

U.S. PATENT DOCUMENTS

| | | |
|---|---|---|
| 5,886,589 A | 3/1999 | Mourant |
| 6,635,055 B1 | 10/2003 | Cronin |
| 7,699,841 B2 | 4/2010 | Carr |
| 7,769,469 B2 | 8/2010 | Carr et al. |
| 8,926,605 B2 | 1/2015 | McCarthy et al. |
| 8,932,284 B2 | 1/2015 | McCarthy et al. |
| 8,961,506 B2 | 2/2015 | McCarthy et al. |
| 8,964,605 B1 | 2/2015 | Ansari |
| 9,226,791 B2 | 1/2016 | McCarthy et al. |
| 9,277,961 B2 | 3/2016 | Panescu et al. |
| 9,861,440 B2 | 1/2018 | Van Der Weide et al. |
| 9,872,729 B2 | 1/2018 | Van Der Weide et al. |
| 9,956,038 B2 | 5/2018 | Allison |
| 11,622,807 B2 | 4/2023 | Crozier et al. |
| 2004/0243004 A1 | 12/2004 | Carr |
| 2004/0249272 A1 | 12/2004 | Carr |
| 2006/0121873 A1 | 6/2006 | Ammar |
| 2009/0187180 A1 | 7/2009 | Brannan |
| 2011/0208177 A1* | 8/2011 | Brannan .............. A61B 18/149 606/33 |
| 2012/0029359 A1 | 2/2012 | Sterzer et al. |
| 2013/0281851 A1 | 10/2013 | Carr |
| 2013/0317499 A1 | 11/2013 | Brannan et al. |
| 2013/0324993 A1 | 12/2013 | McCarthy et al. |
| 2013/0345693 A1 | 12/2013 | Brannan |
| 2014/0303614 A1 | 10/2014 | McCarthy et al. |
| 2015/0290465 A1 | 10/2015 | Mashiach |
| 2016/0030111 A1 | 2/2016 | Ladtkow et al. |
| 2016/0345896 A1 | 12/2016 | Allison |
| 2017/0105798 A1* | 4/2017 | Allison ................ G01K 11/006 |
| 2017/0172655 A1 | 6/2017 | Allison et al. |
| 2018/0078309 A1 | 3/2018 | Van Der Weide et al. |
| 2018/0125579 A1 | 5/2018 | Van Der Weide et al. |
| 2019/0365466 A1 | 12/2019 | Allison |
| 2020/0305974 A1 | 10/2020 | Brannan et al. |
| 2022/0125511 A1 | 4/2022 | Crozier et al. |

FOREIGN PATENT DOCUMENTS

| | | |
|---|---|---|
| EP | 2777591 A1 | 9/2014 |
| EP | 3456279 A1 | 3/2019 |
| JP | 2022089125 A | 6/2022 |
| WO | WO-2006127847 A2 | 11/2006 |
| WO | WO-2007025198 A2 | 3/2007 |
| WO | WO-2010048334 A1 | 4/2010 |
| WO | WO-2010085329 A1 | 7/2010 |
| WO | WO-2010085529 A1 | 7/2010 |
| WO | WO-2012007854 A1 | 1/2012 |
| WO | WO-2013192553 A1 | 12/2013 |
| WO | WO-2014025549 A1 | 2/2014 |
| WO | WO-2014138410 A1 | 9/2014 |
| WO | WO-2015004420 A1 | 1/2015 |
| WO | WO-2016033090 A1 | 3/2016 |
| WO | WO-2016054156 A1 | 4/2016 |
| WO | WO-2016089887 A1 | 6/2016 |
| WO | WO-2016197093 A1 | 12/2016 |
| WO | WO-2017173523 A1 | 10/2017 |
| WO | WO-2017181182 A1 | 10/2017 |
| WO | WO-2018140816 A1 | 8/2018 |
| WO | WO-2019231936 A1 | 12/2019 |
| WO | WO-2020033998 A1 | 2/2020 |
| WO | WO-2020033999 A1 | 2/2020 |
| WO | WO-2020188249 A1 | 9/2020 |
| WO | WO-2022051654 A1 | 3/2022 |

OTHER PUBLICATIONS

International Search Report and Written Opinion dated Aug. 26, 2019 in Int'l PCT Patent Appl. Serial No. PCT/US2019/034226 (0210).

PCT Partial International Search Report dated Apr. 26, 2021 in Int'l PCT Patent Application Serial No. PCT/IB2021/050682 (0310).

* cited by examiner

SYSTEMS AND METHODS FOR MICROWAVE ABLATION AND MEASURING TEMPERATURE DURING ABLATION

CROSS-REFERENCE TO RELATED APPLICATIONS

This application is a continuation of U.S. patent application Ser. No. 16/424,414, filed May 28, 2019, now U.S. Pat. No. 11,337,756, which claims the benefit of priority of U.S. Provisional Patent Application No. 62/678,935, filed May 31, 2018, the entire contents of each of which are incorporated herein by reference.

FIELD OF THE INVENTION

This application generally relates to systems and methods for microwave ablation of target tissue and measuring temperature of the target tissue during ablation.

BACKGROUND OF THE INVENTION

Tissue ablation may be used to treat a variety of clinical disorders and several ablation techniques have been developed, including cryoablation, microwave ablation, radio frequency (RF) ablation, and ultrasound ablation. Numerous treatment schemes affect the nerve using RF power applied by a catheter contacting the inside wall of the artery.

Such techniques are typically performed by a clinician who introduces a catheter having an ablative tip to the target tissue via the venous vasculature, positions the ablative tip adjacent to what the clinician believes to be an appropriate region based on tactile feedback, mapping electrocardiogram (ECG) signals, anatomy, and/or fluoroscopic imaging, actuates flow of an irrigant to cool the surface of the selected region, and then actuates the ablative tip for a period of time believed sufficient to destroy tissue in the selected region.

Although commercially available ablative tips may include thermocouples for providing temperature feedback via a digital display, such thermocouples typically do not provide meaningful temperature feedback during irrigated ablation. For example, the thermocouple only measures surface temperature, whereas the heating or cooling of the tissue that results in tissue ablation may occur at some depth below the tissue surface. Moreover, for procedures in which the surface of the tissue is cooled with an irrigant, the thermocouple will measure the temperature of the irrigant, thus further obscuring any useful information about the temperature of the tissue, particularly at depth. As such, the clinician has no useful feedback regarding the temperature of the tissue as it is being ablated or whether the time period of the ablation is sufficient.

Accordingly, it may only be revealed after the procedure is completed, that the targeted aberrant pathway was not adequately interrupted. In such a circumstance, the clinician may not know whether the procedure failed because the incorrect region of tissue was ablated, because the ablative tip was not actuated for a sufficient period of time to destroy the target tissue, because the ablative tip was not touching or insufficiently touching the tissue, because the power of the ablative energy was insufficient, or some combination of the above. Upon repeating the ablation procedure so as to again attempt to ablate the target tissue, the clinician may have as little feedback as during the first procedure, and thus potentially may again fail to destroy the aberrant pathway. Additionally, there may be some risk that the clinician would re-treat a previously ablated region of the target tissue and not only ablate the target tissue, but damage adjacent tissues.

In some circumstances, to avoid having to repeat the ablation procedure as such, the clinician may ablate a series of regions of the target tissue along which the target tissue is believed to lie, so as to improve the chance of successful ablation. However, there is again insufficient feedback to assist the clinician in determining whether any of those ablated regions are sufficiently destroyed.

U.S. Pat. No. 4,190,053 to Sterzer describes a hyperthermia treatment apparatus in which a microwave source is used to deposit energy in living tissue to effect hyperthermia. The apparatus includes a radiometer for measuring temperature at depth within the tissue, and includes a controller that feeds back a control signal from the radiometer, corresponding to the measured temperature, to control the application of energy from the microwave source. The apparatus alternates between delivering microwave energy from the microwave source and measuring the radiant energy with the radiometer to measure the temperature. As a consequence of this time division multiplexing of energy application and temperature measurement, temperature values reported by the radiometer are not simultaneous with energy delivery.

U.S. Pat. No. 7,769,469 to Carr et al. describes an integrated heating and sensing catheter apparatus for treating arrhythmias, tumors and like, having a diplexer that permits near simultaneous heating and temperature measurement. This patent too describes that temperature measured by the radiometer may be used to control the application of energy, e.g., to maintain a selected heating profile.

Despite the promise of precise temperature measurement sensitivity and control offered by the use of radiometry, there have been few successful commercial medical applications of this technology. One drawback of previously-known systems has been an inability to obtain highly reproducible results due to slight variations in the construction of the microwave antenna used in the radiometer, which can lead to significant differences in measured temperature from one catheter to another. Problems also have arisen with respect to orienting the radiometer antenna on the catheter to adequately capture the radiant energy emitted by the tissue, and with respect to shielding high frequency microwave components in the surgical environment so as to prevent interference between the radiometer components and other devices in the surgical field.

Acceptance of microwave-based hyperthermia treatments and temperature measurement techniques also has been impeded by the capital costs associated with implementing radiometric temperature control schemes. Radiofrequency ablation techniques have developed a substantial following in the medical community, even though such systems can have severe limitations, such as the inability to accurately measure tissue temperature at depth, e.g., where irrigation is employed. However, the widespread acceptance of RF ablation systems, extensive knowledge base of the medical community with such systems, and the significant cost required to changeover to, and train for, newer technologies has dramatically retarded the widespread adoption of radiometry.

U.S. Pat. Nos. 8,926,605 and 8,932,284 to McCarthy et al., the entire contents of each of which are incorporated herein by reference, describe systems for radiometrically measuring temperature during ablation.

In view of the foregoing, it would be desirable to provide systems and methods that permit a high degree of radiometric measurement of temperature at depth in tissue to achieve accurate temperature measurement with microwave heating.

SUMMARY OF THE INVENTION

While there is a breadth of energy based devices to treat a range of conditions, giving promise of improved outcomes, lower risks and shortened recovery times, there remains significant opportunity to exploit capabilities of distinct technologies to deliver optimal therapy to drive outcome and improve risk profiles.

The present invention provides ablation systems and methods for ablating target tissue as well as sensing parameters (e.g., temperature) during ablation. In a preferred embodiment, the ablation systems utilize microwave energy for ablation. For example, the microwave ablation system may include a catheter having a proximal region, a distal region, and at least one lumen extending therebetween, and a switching antenna disposed at the distal region of the catheter. In an exemplary embodiment, the switching antenna includes a main antenna having first and second microwave radiating elements designed to emit microwave energy. In addition, the main antenna is designed to measure a radiometer temperature, e.g., the temperature of the target tissue adjacent the switching antenna, and generate signals indicative of the measured radiometer temperature. The switching antenna further includes a reference termination designed to measure a reference temperature and generate signals indicative of the measured reference temperature, and a switch electrically coupled to the main antenna and the reference termination. For example, the reference termination may be disposed at a junction between the first and second microwave radiating elements. The switch selects between the signals indicative of the measured radiometer temperature from the main antenna and the signals indicative of the measured reference temperature from the reference termination.

Preferably, the ablation systems described herein are configured for minimally invasive introduction into the lungs for ablating target lung tissue through a bronchoscope while sensing temperature at the distal region of the catheter. The target lung tissue may be, for example, tumorous tissue such that the ablative treatment treats lung cancer. The distal region of the catheter may be inserted through the mouth, into the trachea, and into the lung(s) to target tissue(s) for a treatment session. The ablation systems may also be designed to ablate other tissue. For example, efferent and/or afferent nerve fibers surrounding a blood vessel may be ablated for a treatment. As one example, the ablation systems may be intravascularly inserted into the renal artery to ablate the efferent and afferent nerve fibers that surround the renal artery and make up the renal sympathetic nervous system for Renal Denervation (RDN).

In addition, the microwave ablation system may include a generator coupled to the proximal region of the catheter, which provides power to the first and second microwave radiating elements via a cable extending through the at least one lumen of the catheter and coupled to the main antenna at a location proximal to the switch and the reference termination. Further, the microwave ablation system includes a processor that receives the selected signals indicative of the measured radiometer temperature and the selected signals indicative of the measured reference temperature from the switch. The processor may calculate a target tissue temperature based on the signals indicative of the measured radiometer temperature and the signals indicative of the measured reference temperature.

For example, the first and second microwave radiating elements may be a basic dipole and emit microwave energy at a predetermined frequency range (e.g., 1-5 GHz, 2-3 GHz, at or about 2.45 GHz) to the target tissue. The basic dipole may have a cylindrical configuration or a spiral winding configuration. In addition, the first and second microwave radiating elements may include one or more balun transformers designed to transform a single ended transmission line system to a balanced system. For example, a second balun transformer of the one or more balun transformers may be positioned adjacent a first balun transformer of the one or more balun transformers. The one or more balun transformers each may include a thin, flexible dielectric substrate having a top surface and a bottom surface, two conductors printed on the bottom surface, and a single conductor printed on the top surface. For example, the thin, flexible dielectric substrate may have a thickness of at most 0.025 inches, and a dielectric constant on the order of at least 10. The main antenna may be flexible in at least one plane of the substrate. In addition, a foam dielectric may be disposed between regions above and below the thin, flexible dielectric substrate, and the first and second microwave radiating elements.

The switch may include a first switching diode in series connection with a second switching diode. Accordingly, when the first and second switching diodes are closed, a single ended input is transformed to a balanced output that connects to the first and second microwave radiating elements, and the second balun transformer is shorted, thereby transforming to an open circuit at the balanced output. Moreover, when the first and second switching diodes are open, the single ended input is not transformed to the balanced output, thereby forming a straight-through transmission line path to the reference termination. The first and second switching diodes may be microwave PIN diodes, and may be unpackaged and encapsulated, thereby preventing damage as the switching antenna flexes.

The first and second switching diodes may be actuated via a bias source in electrical communication with the first and second switching diodes via the cable. For example, the first and second switching diodes may be actuated to open responsive to a forward current, and to close responsive to a negative voltage. Thus, the reference termination may include a bias blocking capacitor designed to prevent bias current from dissipating in a resistor of the reference termination. Accordingly, the resistor of the reference termination may be located at a distance relative to the first and second microwave radiating elements such that heating of the reference termination is minimized, and wherein the straight-through transmission line path has a same characteristic impedance as a value of the resistor of the reference termination. Moreover, the switching antenna and the generator may operate at the same frequency.

In addition, the system may include a rigid section at the junction between the first and second microwave radiating elements having a length of no more than 5 mm, wherein the switch and the reference termination are disposed on the rigid section. In addition, a thermocouple circuit may be formed by an outer conductor of the cable and a thin dissimilar wire terminating adjacent a resistor of the reference termination. Further, the first microwave radiating element may be coupled to the cable to form a microwave choke, such that the microwave choke provides an open circuit choke between the main antenna and the cable.

In accordance with one aspect of the present invention, the reference termination may be disposed distal to the main antenna such that the reference termination is maintained at body temperature due to blood flow across the reference termination during operation of the microwave ablation system, e.g., during renal denervation treatment.

DETAILED DESCRIPTION OF THE INVENTION

In view of the foregoing, it would be desirable to provide systems and methods for treating living tissue that employs a microwave radiometry system for temperature measurement and control. In accordance with one aspect of the invention, systems and methods are provided for radiometrically measuring temperature during microwave ablation, i.e., calculating temperature based on signal(s) from a radiometer. Unlike standard thermocouple techniques used in existing commercial ablation systems, a radiometer may provide useful information about tissue temperature at depth—where the tissue ablation occurs—and thus provide feedback to the clinician about the extent of tissue damage as the clinician ablates a selected region of the target tissue. Specifically, the present disclosure overcomes the drawbacks of previously-known systems by providing improved systems and methods for microwave ablation of target tissue, and measuring temperature of the target tissue during ablation. The novel invention described herein may have broad application to catheter/probe-based therapies, including but not limited to targets in the vascular system and soft tissue targets in liver, kidney, prostate and lung.

Microwave heating to target tissue and microwave radiometry as a means of monitoring the temperature of the heated tissue ensures that the desired temperatures are delivered to adequately treat the target tissue and achieve therapeutic goals. Specifically, heating and temperature sensing is accomplished with a catheter using a single antenna which is shared for both functions. The microwave heating may be directed toward the target tissue. A radiometer, operating at the same frequency and time sharing the antenna with the microwave generator, senses the microwave emissions from the region surrounding the antenna and converts these to tissue temperature. In this case, the volume of tissue being monitored includes, e.g., tumorous lung tissue. An algorithm relates the temperature at the target region to the volume temperature reading.

Figure 1:
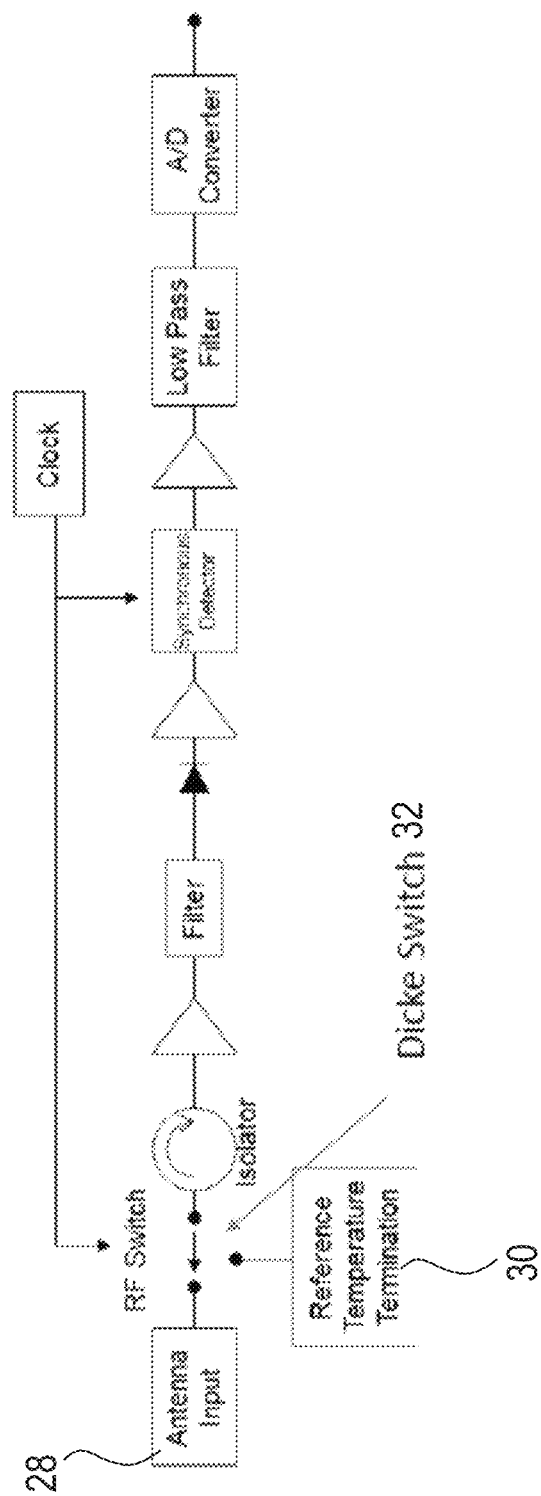
FIG. 1 is a simplified block diagram of a microwave radiometer having a Dicke switch.

However, there are obstacles to achieving accurate temperature measurement using radiometry with microwave heating. These result from the dissipative losses in the relatively long coaxial cable between the radiometer and the antenna. The usual approach uses a Dicke radiometer which compares the unknown temperature of the target tissue being heated to an internal reference of known temperature in the radiometer. FIG. 1 illustrates a simplified block diagram of such a system having a Dicke radiometer. As shown in FIG. 1, an input switch, e.g., Dicke switch 32, is used that selects either antenna input 28 or an internal reference input, e.g., reference temperature termination 30. The approach is popular because everything in the measurement path behind Dicke switch 32 is common to both the target measurement from antenna input 28 and the reference measurement from reference temperature termination 30, and most of the possible measurement errors drop out of the calculations.

The problem with antenna catheters is the dissipative loss in the coaxial cable running the length of the catheter. The emissions resulting from the cable losses are indistinguishable from the emissions received by the antenna. The radiometer measures the antenna temperature combined with the cable temperature. The problem is aggravated by the desire for small diameter catheters requiring high loss, small diameter coaxial cables, and heating of the coaxial cable caused by dissipation of some of the generator power.

Figure 2:
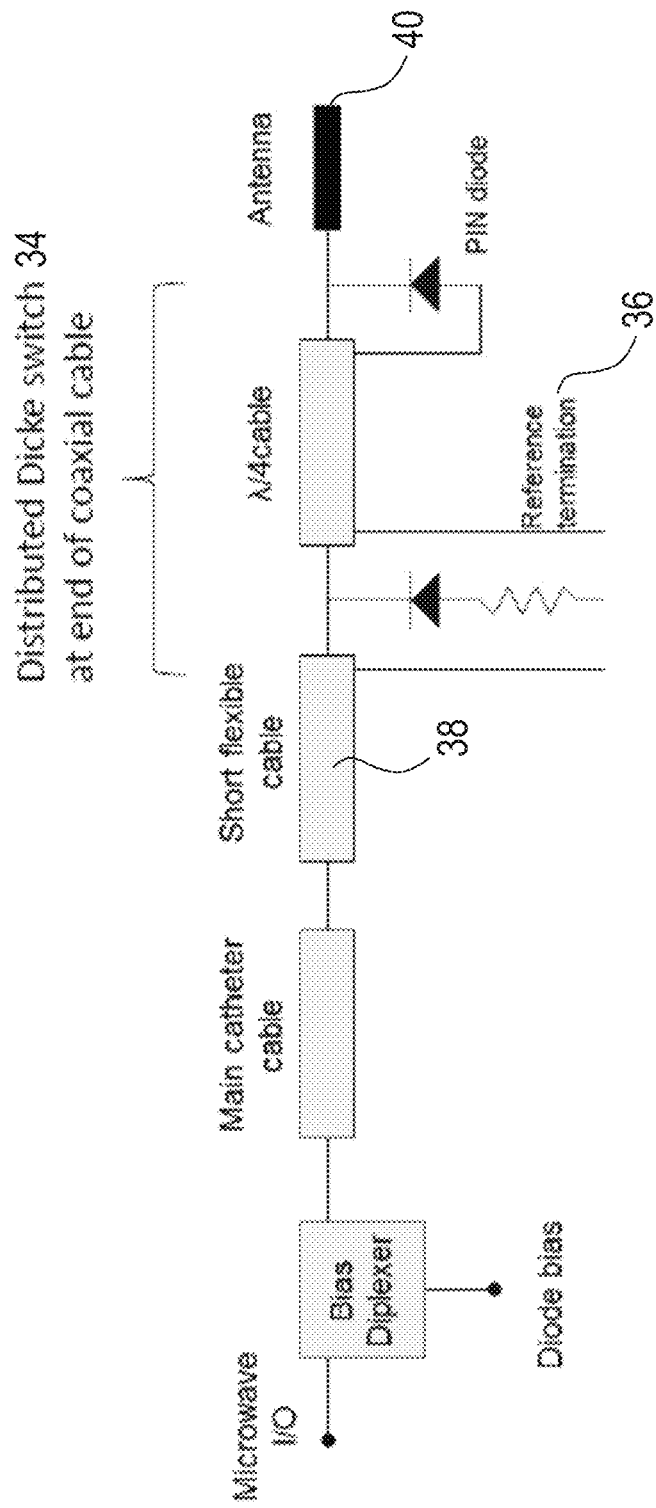
FIG. 2 is a block diagram of a microwave heating and temperature sensing system where the Dicke switch and reference termination are disposed at the end of the coaxial cable near the connection to the antenna.

A solution is disclosed in the block diagram of FIG. 2. As illustrated in FIG. 2, Dicke switch 34 and reference termination 36 have been moved out to the end of the coaxial cable, e.g., short flexible cable 38 at the distal end of the main catheter cable, near the connection to antenna 40. Now the coaxial cable is part of both the target measurement from antenna 40 and the reference measurement from reference termination 36, and heat dissipating therefrom drops out of the temperature calculation. However, the scheme is subject to some error resulting from heating of the reference due to its proximity to the heating cable.

Figure 3:
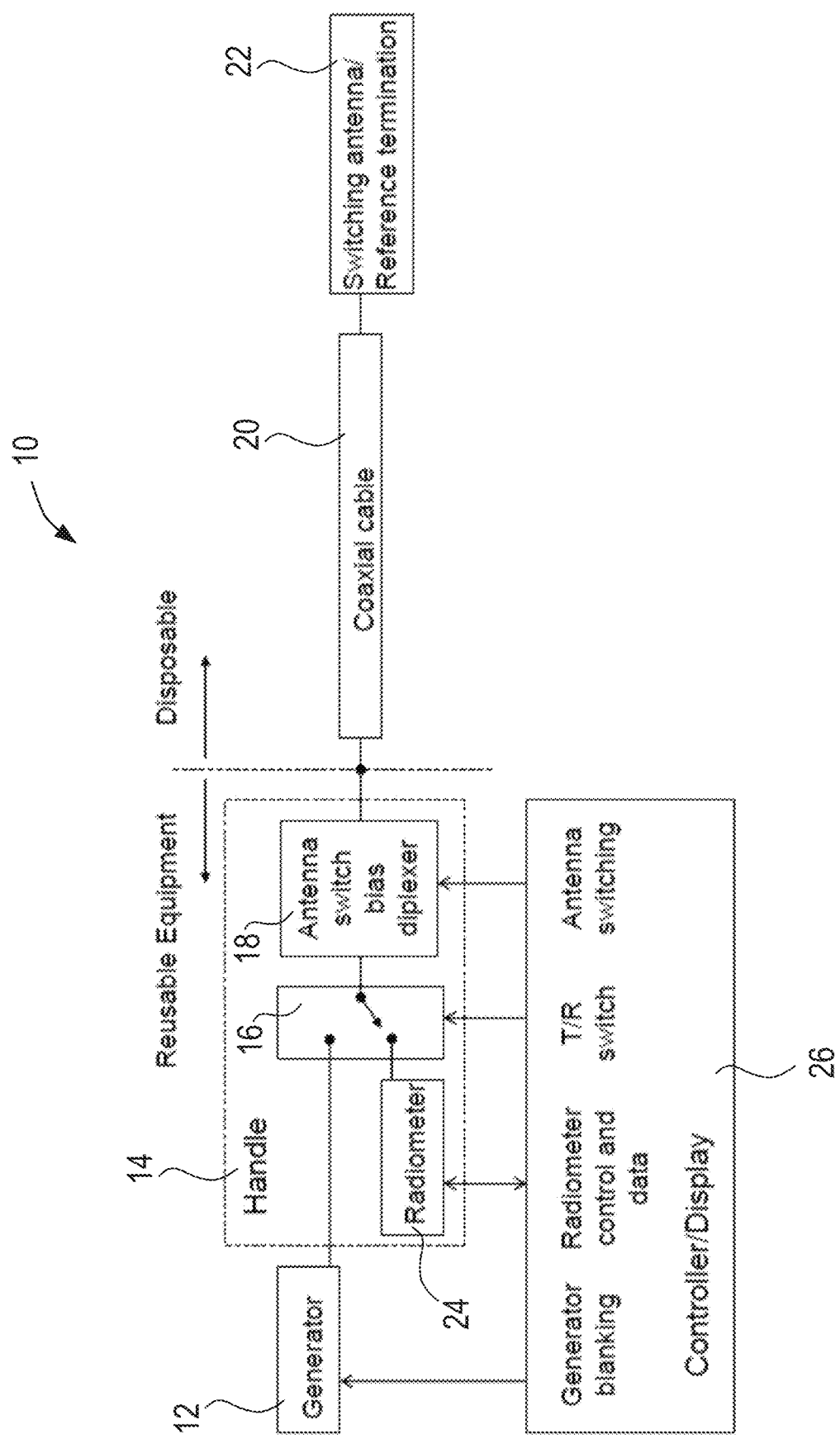
FIG. 3 is a block diagram of an exemplary microwave ablation system constructed in accordance with the principles of the present invention.

To overcome the drawbacks of previously-known radiometry systems, the present invention integrates the Dicke switch radiometer function integrated into the antenna. For example, referring now to FIG. 3, a block diagram illustrating microwave heating and temperature sensing system 10 constructed in accordance with the principles of the present invention is provided. As shown in FIG. 3, generator 12 supplies ablative energy to switching antenna 22 through Transmit/Receive (T/R) switch 16 followed by antenna switch bias diplexer 18. Generator 12 may be any previously-known commercially available ablation energy generator, e.g., a microwave energy generator, thereby enabling radiometric techniques to be employed with reduced capital outlay.

Further, radiometer 24 receives temperature measurements from switching antenna 22 via cable 20, e.g., coaxial cable. Switching antenna 22 includes a main antenna having one or more microwave radiating elements for emitting microwave energy and for measuring temperature of tissue adjacent the main antenna, and a reference termination for measuring a reference temperature. In addition, switching antenna 22 includes a switching network, e.g., a Dicke switch, integrated therein for detecting the volumetric temperature of tissue subjected to ablation. The switching network selects between the signals indicative of measured radiometer temperature from the main antenna of switching antenna 22, e.g., the temperature of the tissue adjacent the main antenna during the ablation procedure, and signals indicative of the measured reference temperature from the reference termination of switching antenna 22. As the switching network is integrated within switching antenna 22, and sufficiently far from the connection point of cable 20 and switching antenna 22, heating of the reference termination by cable 20 is avoided.

Switch 16 and antenna switch bias diplexer 18 may be disposed within handle 14, along with radiometer 24 for receiving temperature measurements from switching antenna 22 depending the state of switch 16. For example, switch 16 may be in an ablation state such that microwave power may be transmitted from generator 12 to switching antenna 22, or switch 16 may be in a measurement state such that radiometer 24 may receive temperature measurement from switching antenna 22, e.g., from the main antenna and/or the reference termination. Handle 14 may be reusable, while cable 20 and switching antenna 22 may be disposable.

System 10 further includes controller 26 coupled to generator 12 and switching antenna 22 via, e.g., handle 14 and cable 20, to coordinate signals therebetween. Controller 26 thereby provides generator 12 with the information required for operation, transmits ablative energy to switching antenna 22 under the control of the clinician, and may display via a temperature display the temperature at depth of tissue as it is being ablated, for use by the clinician. The displayed temperature may be calculated based on signal(s) measured by switching antenna 22 using computer algorithms. Thus, controller 26 includes a processor having memory for storing instructions to be executed by controller 26.

For example, the processor may receive signals indicative of measured radiometer temperature from the main antenna of switching antenna 22, e.g., the temperature of the tissue adjacent switching antenna 22 during the ablation procedure, and signals indicative of the measured reference temperature from the reference termination of switching antenna 22, such that the processor may calculate the volumetric temperature of the tissue subject to ablation based on the signals. In addition, the processor may direct switch 16 to move between the ablation state and the measurement state as described above.

The microwave power propagates from generator 12 down cable 20 in the catheter to switching antenna 22 at the catheter tip. The microwave power radiates outward from the main antenna of switching antenna 22 into the target tissue (e.g., target lung tissue such as a tumor). In other examples, such as where the ablation system is used for denervation, an introducer device may be used to deliver the catheter within the body lumen, and a spacer device may be used to ensure that switching antenna 22 is deployed in the approximate center of the body lumen. The volume of blood flowing through the body lumen at body temperature may cool the surface of the body lumen in immediate contact with the blood. In addition to, or alternatively, coolant from outside the body, introduced through a coolant lumen of the catheter may be used to cool the surface of the surface of the body lumen. Tissue beyond the lumen wall, that does not experience this cooling, heats up. Sufficient microwave power is supplied to heat the target tissue (e.g., nerve area) to a temperature that destroys the target tissue.

Figures 4A, 4B:
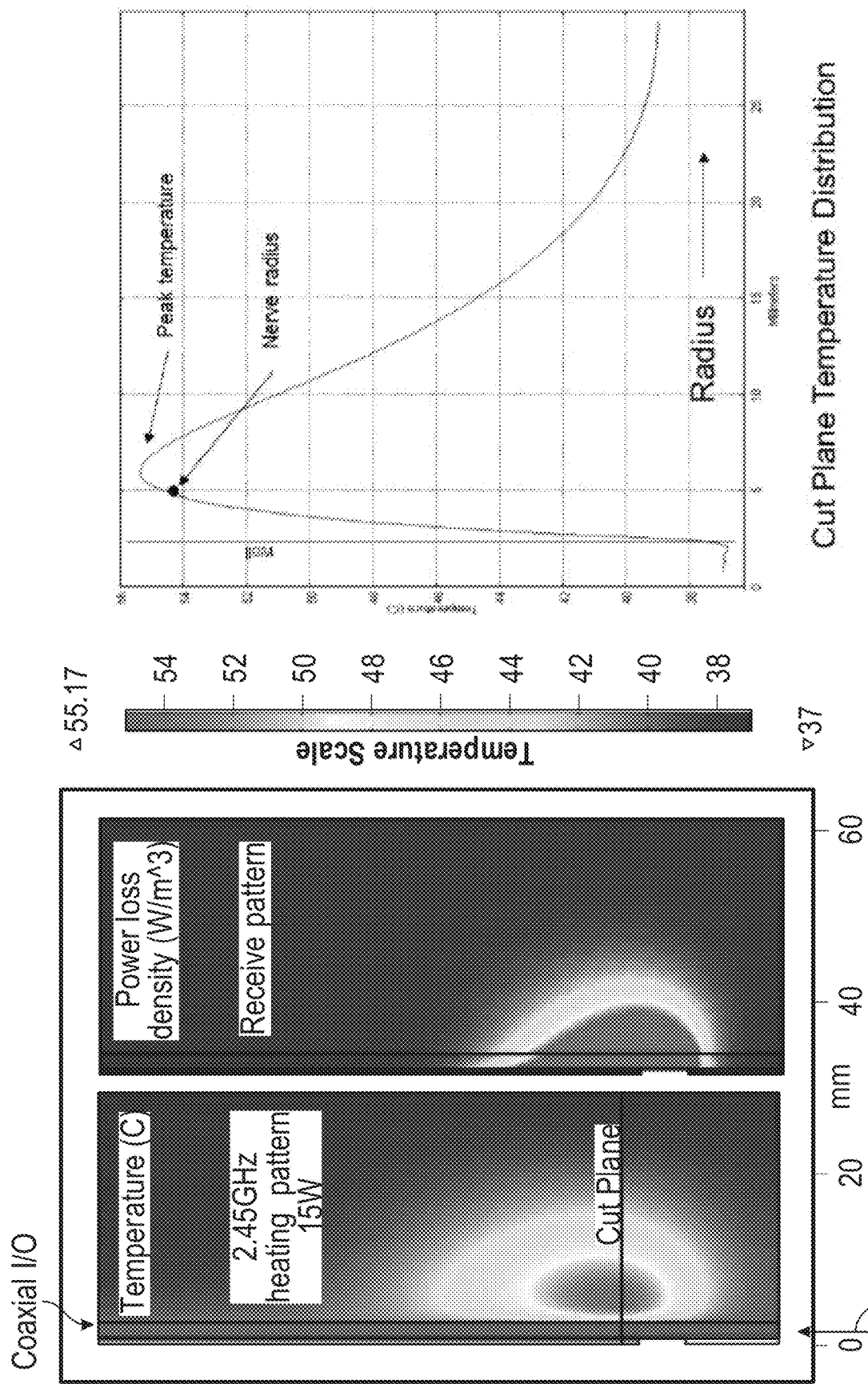
FIG. 4A illustrates a computer simulation of the temperature field and power loss density created by the microwave heating of the system of FIG. 3.
FIG. 4B illustrates the cut plane temperature distribution.

A computer simulation of the temperature field created by microwave heating is shown in FIG. 4. FIG. 4 illustrates a cut through the switching antenna and surrounding tissue. The effect is symmetrical around the antenna so just one half of the cut plane is shown. The temperature along a radial line through the peak temperature shows the temperature within the target tissue. The temperature rises inside the tissue near the tissue surface and reaches a maximum at a depth near the target tissue. FIG. 4 also illustrates the microwave power loss density pattern perceived by the switching antenna. Since the switching antenna and frequency are common to both the generator and radiometer, the patterns produced for both functions are coincident and the radiometer optimally monitors the heated region.

Figure 5A:
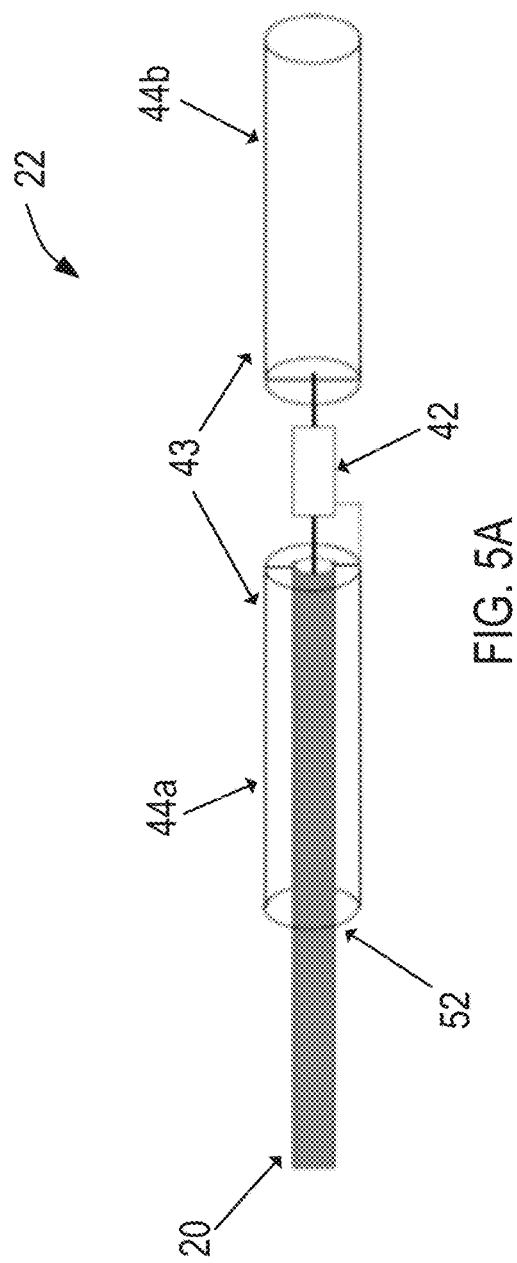
FIG. 5A illustrates an exemplary microwave ablation system where the reference termination is disposed between the dipoles of the radiometer antenna.
Figure 5B:
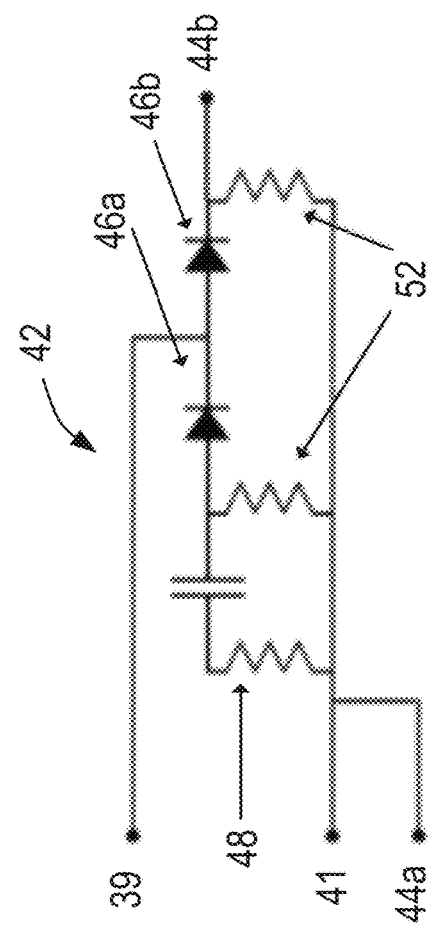
FIG. 5B illustrates the switching network of the microwave ablation system of FIG. 5A.

Referring now to FIGS. 5A and 5B, switching antenna 22 of microwave ablation system 10 is provided. Switching antenna 22 includes main antenna 43 that is used for both microwave heating and temperature sensing, and reference termination 48 for measuring a reference temperature, e.g., temperature adjacent switching antenna 22. For example, main antenna 43 of switching antenna 22 includes one or more microwave radiating elements, e.g., first microwave radiating element 44a and second microwave radiating element 44b, that are designed to receive power from generator 12 via cable 20, and to emit microwave energy into the surrounding target tissue at a level sufficient to ablate the target tissue.

Main antenna 43 of switching antenna 22 further includes means for detecting microwave emissions from the region surrounding the antenna, e.g., one or more circuits formed by microwave radiating elements 44a, 44b, and converts these to temperature of the tissue adjacent switching antenna 22, i.e., radiometer temperature. Switching antenna 22 further includes reference termination 48 for measuring a reference temperature. In addition, switching antenna 22 integrates switching network 42, e.g., a Dicke switch, disposed between the dipole halves of microwave radiating elements 44a, 44b of main antenna 43 of switching antenna 22.

The volume temperature output will be the difference between the radiometer temperature, e.g., the temperature of the tissue heated surrounding main antenna 43, and the reference temperature measured by reference termination 48. The volume temperature output may be calculated based on signals indicative of the measured radiometer temperature from microwave radiating elements 44a, 44b of main antenna 43 and the signals indicative of the measured reference temperature from reference termination 48 using algorithms, such as those described in U.S. Pat. Nos. 8,932,284 and 8,926,605, both of which are incorporated herein by reference.

Specifically, all of the switching components, e.g., switching diodes 46a, 46b, and reference termination 48 are located at the junction of the two antenna dipole halves. The junction between the two antenna dipole halves may have a length of, e.g., no more than 5 mm, and preferably no more than 3 mm. Accordingly, the integrated antenna/switch configuration of microwave ablation system 10 is physically shorter and more flexible. Switching diodes 46a, 46b are actuated by biasing switching diodes 46a, 46b ON or OFF, and are switched to the same state in unison. Accordingly, only a single bias source is required and may be operatively coupled to switching diodes 46a, 46b via conductors of cable 20. Switching diodes 46a, 46b may be, e.g., microwave PIN diodes, and are biased with a small forward current in the ON state or back biased with a negative voltage in the OFF state.

In addition, microwave choke arrangement 52 is provided to minimize fold back of the radiating pattern of microwave energy from microwave radiating elements 44a, 44b onto the coaxial catheter shaft. The choke is formed by connecting the proximal dipole half, e.g., microwave radiating element 44a, to cable 20 at the feed point of main antenna 43. A coaxial structure is formed between microwave radiating element 44a and cable 20 which results in the open circuit choke between main antenna 43 and cable 20.

Input from main antenna 43 or from reference termination 48 is selected by reversing the polarity of the bias current applied to center conductor 39 of cable 20. The series-connected switching diodes 46a, 46b are either a small resistance that passes the microwave signal or a small capacitance blocking the signal depending on the bias polarity. Resistors, e.g., bias components 52, return the bias current through outer conductor 41 of cable 110. A bias current diplexer supplies the bias to the proximal end of the catheter outside the body.

The chip level switching components (diodes, resistors and capacitor) are very small and reside on a ceramic card in the short space between the dipole halves of microwave radiating elements 44a, 44b. Cable 20 and the antenna structures are formed of flexible materials that may navigate through tight passages. The only rigid section may be switching network 42, which is no longer than about 3 mm.

System 10 is suitable for applications such as ablation of lung tissue where reference termination 48 must establish a reference temperature. For this reason, reference termination 48 is located on the proximal side of the antenna structure so that a temperature sensor does not have to cross the feed point of main antenna 43 which may disrupt the antenna radiating pattern. A thermocouple circuit formed by outer conductor 41 and a very thin dissimilar metal wire terminating near the reference resistor of reference termination 48 may be used for this purpose.

Figure 6:
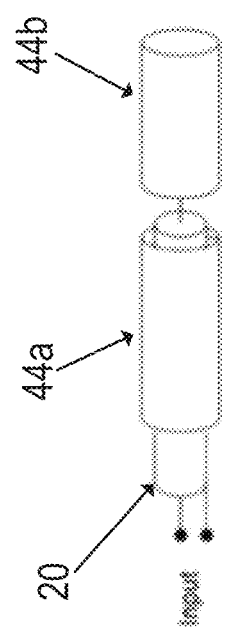
FIG. 6 illustrates a basic dipole of the microwave radiating elements of an exemplary microwave ablation system constructed in accordance with the principles of the present invention.
Figure 7:
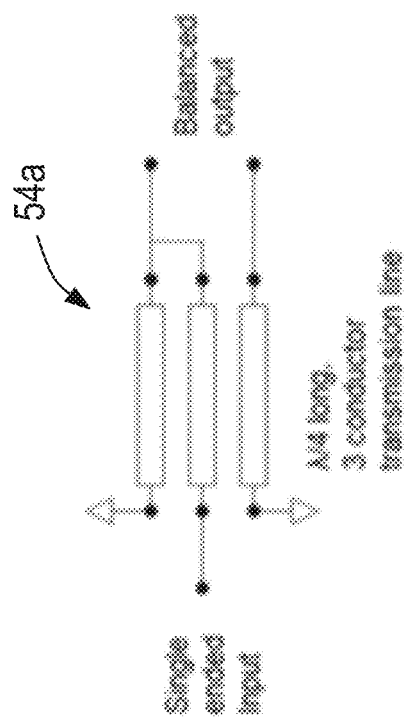
FIG. 7 illustrates a balun transformer of the microwave radiating elements of the exemplary microwave ablation system in accordance with the principles of the present invention.

As illustrated in FIG. 6, microwave radiating elements 44a, 44b are a basic dipole that receives power from generator 12 via cable 20. As shown in FIG. 6, microwave radiating elements 44a, 44b may have a cylindrical shape. As will be understood by a person having ordinary skill in the art, microwave radiating elements 44a, 44b may have other shapes including a spiral winding. Within each of microwave radiating elements 44a, 44b is a balun transformer. The balun transformer transforms a single ended transmission line system to a balance system as shown in FIG. 7, which illustrates balun transformer 54a.

Figure 8:
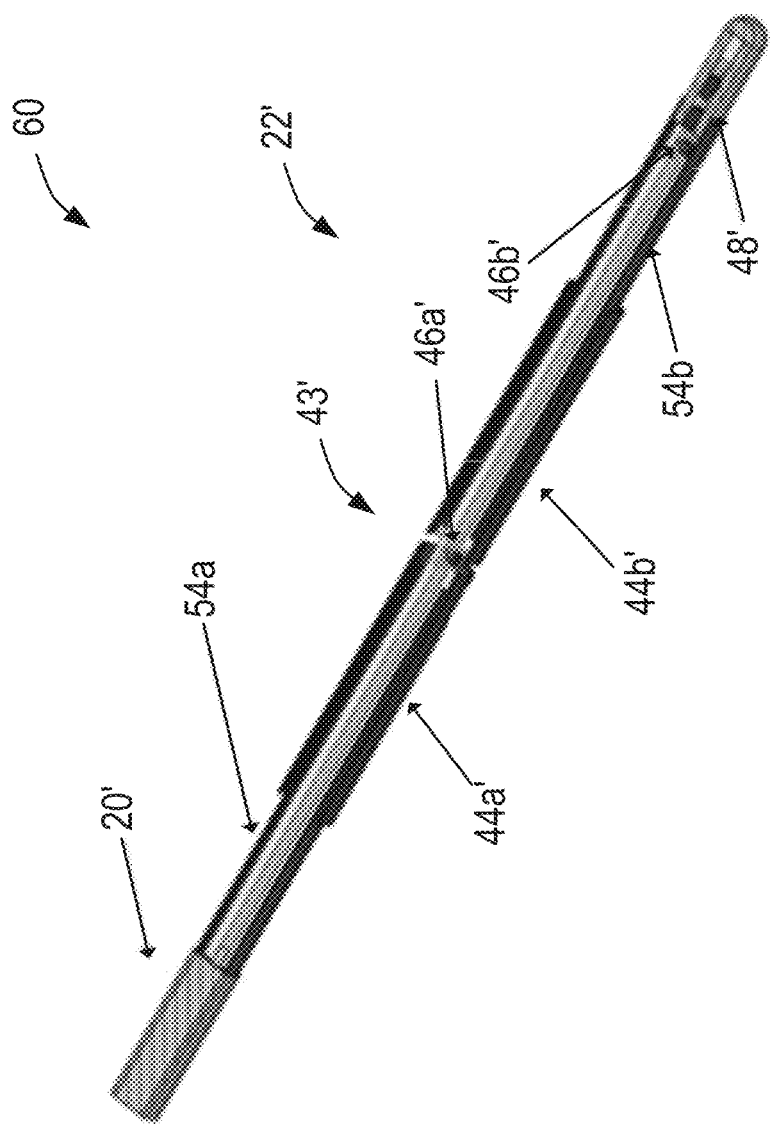
FIG. 8 is a cut away view of a radiometer antenna of the exemplary microwave ablation system constructed in accordance with the principles of the present invention.

Referring now to FIG. 8, alternative exemplary microwave ablation system 60 is provided. Microwave ablation system 60 is constructed similarly to microwave ablation system 10 of FIG. 3 wherein like components are identified by like-primed reference numbers. For example, cable 20' corresponds with cable 20, switching antenna 22' corresponds with switching antenna 22, main antenna 43' corresponds with main antenna 43, microwave radiating elements 44a', 44b' correspond with microwave radiating elements 44a, 44b, switching diodes 46a', 46b' correspond with switching diodes 46a, 46b, and reference termination 48' corresponds with reference termination 48. As shown in FIG. 8, within each of microwave radiating elements 44a, 44b is balun transformer 54a, 54b, respectively.

Microwave ablation system 60 differs from microwave ablation system 10 in that reference termination 48' is disposed distal to second microwave radiating element 44b'. Specifically, switching antenna 22' integrates a switching network, e.g., a Dicke switch including switching diodes 46a', 46b', into main antenna 43' which allows reference termination 48' to protrude out from the distal end of main antenna 43'. Accordingly, system 60 may be used in applications such as renal denervation where reference termination 48' may be maintained at body temperature by blood flow.

The structure of main antenna 43' is unique in that it integrates a radiometer Dicke switch function into a flexible remote antenna and provides for radiometer reference termination 48' to protrude from main antenna 43' into a stable temperature region, e.g., path of blood flow. The volume temperature output will be the difference between the radiometer temperature, e.g., the temperature of the tissue heated surrounding main antenna 43' and the reference temperature, e.g., known stable body temperature provided by blood flow over reference termination 48', e.g., in the renal artery. The volume temperature output may be calculated based on signals indicative of the measured radiometer temperature from microwave radiating elements 44a', 44b' of main antenna 43' and the signals indicative of the measured reference temperature from reference termination 48' using algorithms, such as those described in U.S. Pat. Nos. 8,932,284 and 8,926,605, both of which are incorporated herein by reference.

Figure 9A:
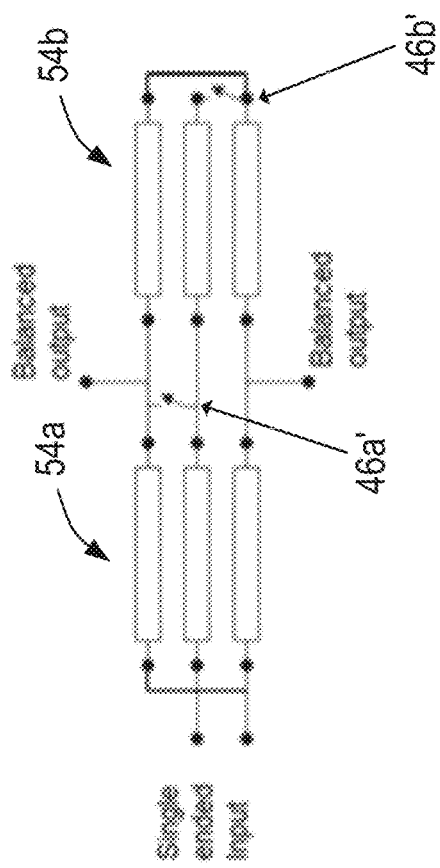
FIG. 9A illustrates back to back balun transformers of the microwave radiating elements of the exemplary microwave ablation system constructed in accordance with the principles of the present invention.
Figure 9B:
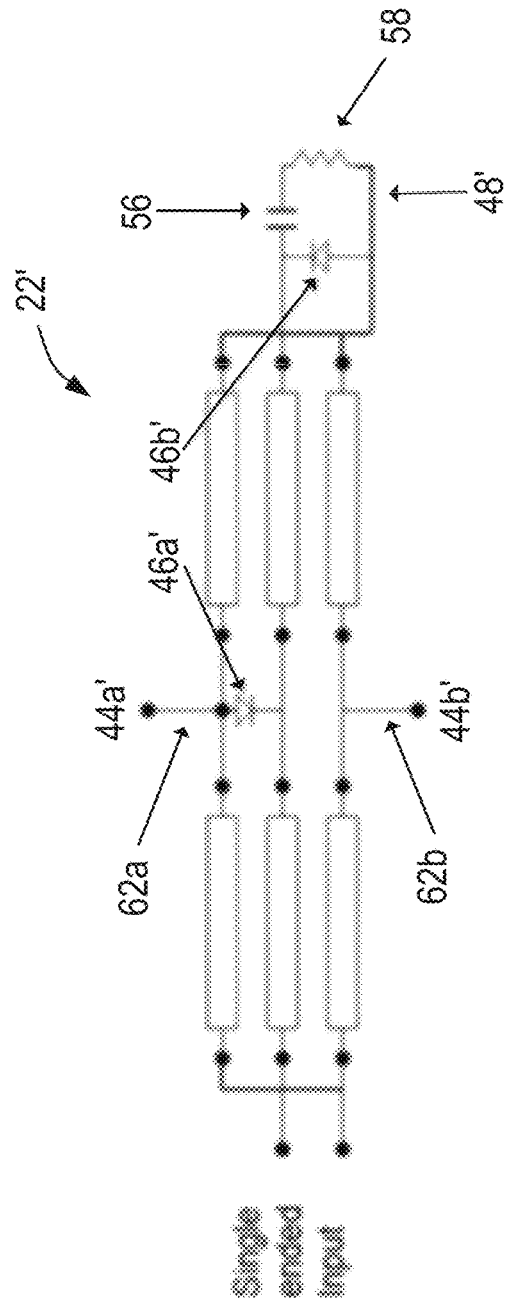
FIG. 9B illustrates the back to back balun transformers of FIG. 9A with switching diodes and a reference termination resistor in accordance with the principles of the present invention.

As illustrated in FIG. 9A, microwave radiating elements 44a', 44b' include two back to back balun transformers 54a, 54b. As shown in FIG. 9B, two switching diodes, e.g., switching diodes 46a', 46b', are integrated within microwave radiating elements 44a', 44b' of main antenna 43'. Switching diode 46a' is positioned between balun transformers 54a, 54b, and switching diode 46b' is positioned distal to balun transformer 54b, e.g., between balun transformer 54b and reference termination 48' (not shown). When switching diodes 46a', 46b' are closed, the single ended input is transformed to the balanced output that connects to microwave radiating elements 44a', 44b'. Balun transformer 54a is shorted at the distal end of main antenna 43', and therefore, transforms to an open circuit at the balanced output. When switching diodes 46a', 46b' are open as shown in FIG. 9A, the transformation is not made and the structure becomes a straight through transmission line path to the distal end of main antenna 43' where the reference termination, e.g., reference termination 48', is located as illustrated in FIG. 9B.

FIG. 9B illustrates switching antenna 22' having back to back balun transformers 54a, 54b, with switching diodes 46a', 46b' integrated therein, and reference termination 48' having bias blocking capacitor 56 and reference termination resistor 58. As further shown in FIG. 9B, connection 62a connects to microwave radiating element 44a', and connection 62b connects to microwave radiating element 44b'. Switching diodes 46a', 46b' are actuated by biasing switching diodes 46a', 46b' ON or OFF, and are switched to the same state in unison. Accordingly, only a single bias source is required and may be operatively coupled to switching diodes 46a', 46b' via conductors of cable 20.

Switching diodes 46a', 46b' may be, e.g., microwave PIN diodes, and are biased with a small forward current in the ON state or back biased with a negative voltage in the OFF state. Bias blocking capacitor 56 prevents bias current from dissipating in reference termination resistor 58 of reference termination 48'. Reference termination resistor 58 may be located any distance from balun transformers 54a, 54b of microwave radiating elements 44a', 44b' to minimize heating of reference termination 48' as long as the connecting transmission line is of the same characteristic impedance as the resistor value of reference termination resistor 58.

Figure 10B:
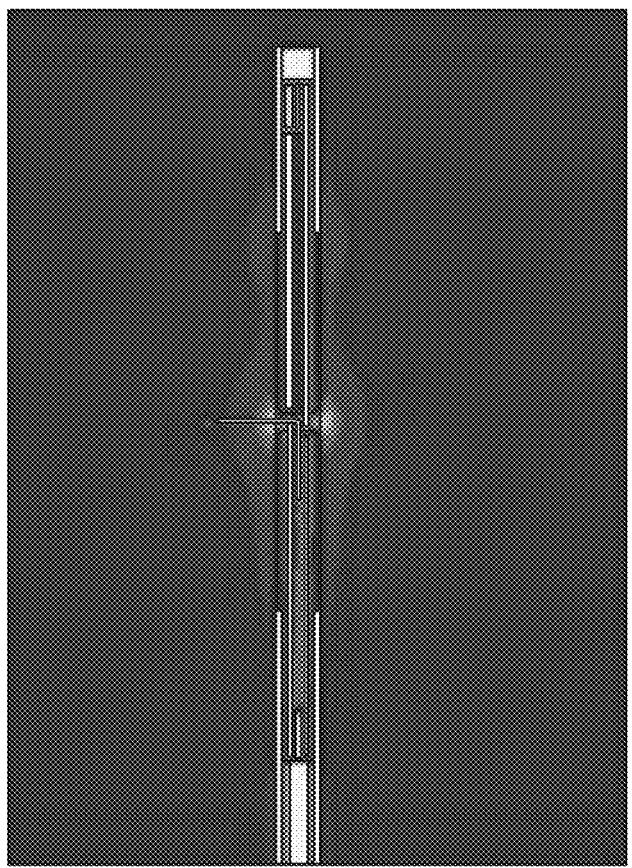
FIG. 10A illustrates the power dissipation in the tissue when the diodes of the exemplary microwave ablation system are biased ON, and FIG. 10B illustrates the power dissipation in the tissue when the diodes of the exemplary microwave ablation system are biased OFF.
Figure 10A:
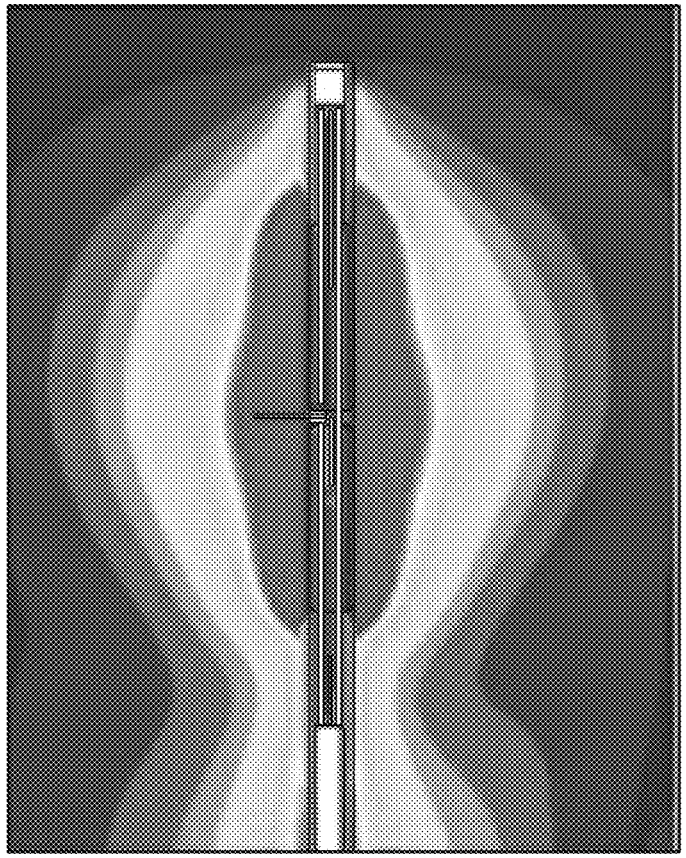

Referring now to FIGS. 10A and 10B, antenna power loss density patterns for both switch positions of switching diodes 46a', 46b', e.g., ON and OFF, is provided. For example, FIG. 10A illustrates power dissipation in the tissue during operation of switching antenna 22' when switching diodes 46a', 46b' are biased ON. As shown in FIG. 10A, a volume of tissue at a predetermined depth within the target tissue, e.g., where the target tissue to be ablated is located, is heated to the desired temperature sufficient for ablation. FIG. 10B illustrates power dissipation in the tissue when switching diodes 46a', 46b' are biased OFF, and thus no dissipation is shown indicating that switching antenna 22' is detecting only reference termination 48'.

Figure 11:
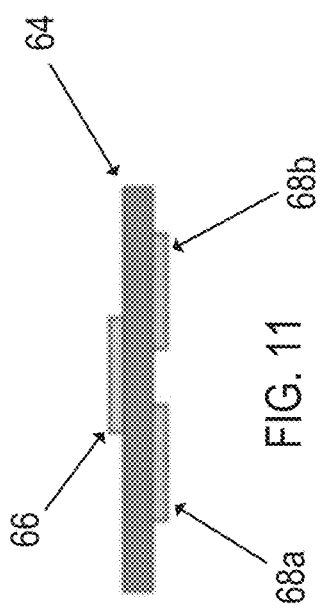
FIG. 11 is a cross-section of a three conductor transmission line of the balun transformer constructed in accordance with the principles of the present invention.

To overcome the challenge of constructing the balun structure and mounting the switching diodes in a flexible, small diameter catheter, a three conductor transmission line structure is used to form balun transformers 54a, 54b as shown in FIG. 11. As illustrated in FIG. 11, thin, flexible dielectric substrate 64 includes center conductor 66 printed on the top surface of substrate 64, and two split ground conductors 68a, 68b printed on the bottom surface of substrate 64. Substrate 64 may be, for example, at most 0.005" thick, and preferably up to 0.005 inches thick. In addition, the dielectric constant of substrate 64 is relatively high, e.g., on the order of at least 10. Transmission line impedance is a function of widths of the conductors and the size of the gap between split ground conductors 68a, 68b.

Figure 12:
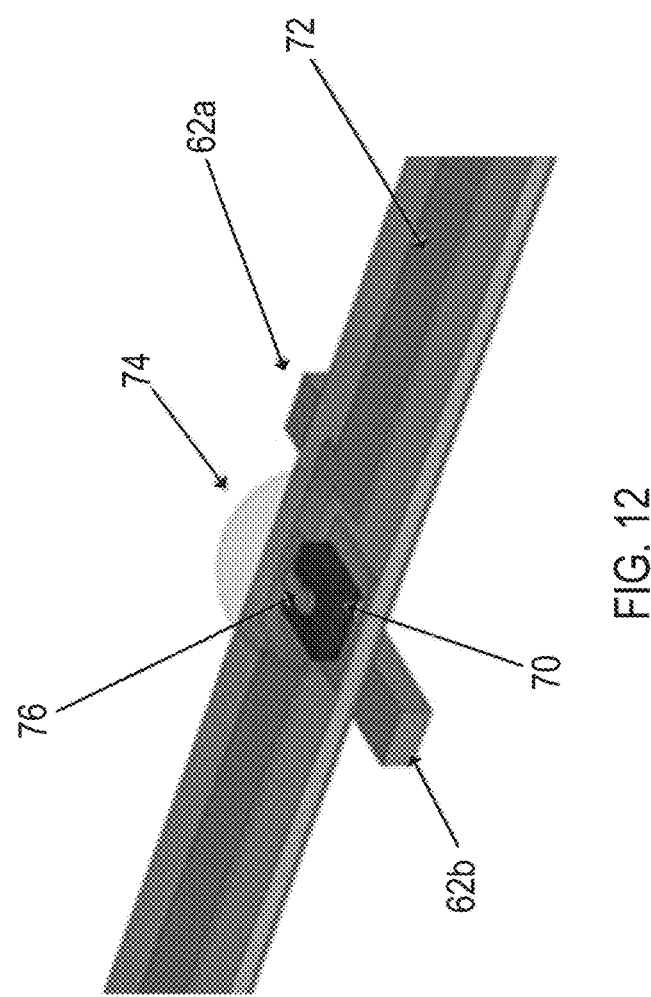
FIG. 12 illustrates encapsulated unpackaged diodes of the exemplary microwave ablation system in accordance with the principles of the present invention.

Switching antenna 22' may need to flex during delivery to the target tissue site, e.g., to make the turn from the femoral artery into the renal artery. To keep the geometry of switching antenna 22' small, unpackaged diodes are used and are encapsulated to prevent damage as main antenna 43' flexes. For example, FIG. 12 illustrates diode chip 70 and ribbon connection 76 positioned on top side circuit trace 72, and encapsulant 74. In addition, FIG. 12 illustrates connection 62a which connects to microwave radiating element 44a', and connection 62b which connects to microwave radiating element 44b'.

In an embodiment where main antenna 43' is stiff in one plane of the substrate, main antenna 43' has flexibility in at least one plane such that it may navigate, e.g., the bends in the arteries of the patient. For example, main antenna 43' may be relatively stiff in the plane of substrate 64 but may curl in the plane perpendicular to substrate 64. This is judged to be adequate flexibility requiring only that the catheter be twisted to orient it with the direction of the required bend. Thus, the structure of main antenna 43' allows main antenna 43' to be flexible in at least one plane, and preferably in both planes. A foam dielectric may be used to fill the regions above and below substrate 64 under microwave radiating elements 44a', 44b'. A braided metal shield layer may also be used to cover balun transformers 54a, 54b under microwave radiating elements 44a', 44b'.

While various illustrative embodiments of the invention are described above, it will be apparent to one skilled in the art that various changes and modifications may be made herein without departing from the invention. It will further be appreciated that the systems and methods described herein may be utilized for ablation and temperature measurements of tissue other than the renal artery. The appended claims are intended to cover all such changes and modifications that fall within the true spirit and scope of the invention.

What is claimed is:

1. A method for monitoring microwave ablation of target tissue, the method comprising:
   emitting, by proximal and distal microwave radiating elements of a switching antenna, microwave energy to target tissue;
   measuring, by the switching antenna, a radiometer temperature and generating signals indicative of the measured radiometer temperature;
   measuring, by a reference termination disposed between the proximal and distal microwave radiating elements, a reference temperature and generating signals indicative of the measured reference temperature;
   receiving, by a processor, the signals indicative of the measured radiometer temperature and the signals indicative of the measured reference temperature from a switch configured to select between the signals generated by the switching antenna and the signals generated by the reference termination; and
   calculating, by the processor, a target tissue temperature based on the signals indicative of the measured radiometer temperature and the signals indicative of the measured reference temperature.

2. The method of claim 1, wherein emitting microwave energy to the target tissue comprises emitting microwave energy within a range of 1-5 GHz to the target tissue.

3. The method of claim 1, wherein emitting microwave energy to the target tissue comprises providing, by a generator operatively coupled to the switching antenna, power to the switching antenna to cause the proximal and distal microwave radiating elements to emit microwave energy.

4. The method of claim 3, wherein the generator is operatively coupled to the switching antenna via a cable coupled to the switching antenna at a location proximal to the switch and the reference termination.

5. The method of claim 4, wherein the proximal microwave radiating element is coupled to the cable to form a microwave choke, the microwave choke providing an open circuit choke between the switching antenna and the cable to minimize fold back of a radiating pattern of microwave energy from the proximal and distal microwave radiating elements.

6. The method of claim 1, wherein the proximal and distal microwave radiating elements comprise a basic dipole.

7. The method of claim 1, wherein the proximal and distal microwave radiating elements comprise one or more balun transformers configured to transform a single ended transmission line system to a balanced system.

8. The method of claim 7, wherein a second balun transformer of the one or more balun transformers is positioned adjacent a first balun transformer of the one or more balun transformers.

9. The method of claim 8, wherein the switch comprises a first switching diode in series connection with a second switching diode.

10. The method of claim 9, further comprising actuating, by a bias source in electrical communication with the first and second switching diodes, the first and second switching diodes by applying a negative voltage to close the first and second switching diodes to transform a singled ended input to a balanced output that connects to the proximal and distal microwave radiating elements, and to short the second balun transformer, thereby transforming to an open circuit at the balanced output.

11. The method of claim 9, further comprising actuating, by a bias source in electrical communication with the first and second switching diodes, the first and second switching diodes by applying a forward current to open the first and second switching diodes to prevent transformation of a single ended input to a balanced output, thereby forming a straight-through transmission line path to the reference termination.

12. The method of claim 9, further comprising preventing, by a bias blocking capacitor of the reference termination, bias current from dissipating in a resistor of the reference termination.

13. The method of claim 12, wherein the resistor of the reference termination is located at a distance relative to the proximal and distal microwave radiating elements such that heating of the reference termination is minimized, and wherein the straight-through transmission line path comprises a same characteristic impedance as a value of the resistor of the reference termination.

14. The method of claim 1, wherein the switch is disposed between the proximal and distal microwave radiating elements.

15. The method of claim 1, wherein the switch is configured to select between the signals generated by the switching antenna and the signals generated by the reference termination by reversing a polarity of a bias current applied to a center conductor of a cable coupled to the switching antenna.

16. The method of claim 1, wherein calculating the target tissue temperature comprises calculating, by the processor, volumetric temperature of the target tissue based on the signals indicative of the measured radiometer temperature and the signals indicative of the measured reference temperature.

17. The method of claim 1, wherein the switching antenna is disposed on the distal region of a catheter, the method further comprising delivering, by an introducer device, the catheter to a target site within a patient such that the switching antenna is positioned adjacent to the target tissue.

18. The method of claim 1, further comprising directing, by the processor, the switch to move between an ablation state where microwave energy is emitted by the switching antenna, and a measurement state where radiometer temperature and reference temperature are measured by the switching antenna and the reference termination, respectively.

19. The method of claim 1, further comprising displaying the target tissue temperature during microwave ablation of the target tissue.

20. The method of claim 1, further comprising adjusting the emission of microwave energy to the target tissue based on the calculated target tissue temperature.

21. The method of claim 1, further comprising, prior to emitting microwave energy to the target tissue, introducing a catheter comprising the switching antenna to lung tissue in a minimally invasive manner for ablating target lung tissue.

22. The method of claim 21, wherein the catheter is introduced through a bronchoscope.

23. The method of claim 21, wherein the target lung tissue is tumorous tissue such that an ablative treatment treats lung cancer.

24. The method of claim 21, wherein a distal region of the catheter is introduced through a mouth, into a trachea, and into a lung to the target lung tissue for ablation.

\* \* \* \* \*